United States Patent
Wostyn

(10) Patent No.: US 10,980,437 B2
(45) Date of Patent: Apr. 20, 2021

(54) BIOMARKERS FOR VISUAL IMPAIRMENT AND INTRACRANIAL PRESSURE (VIIP) SYNDROME

(71) Applicant: P&X MEDICAL NV, Oostkamp (BE)

(72) Inventor: Peter Wostyn, Oostduinkerke (BE)

(73) Assignee: P&X MEDICAL NV, Oostkamp (BE)

( * ) Notice: Subject to any disclaimer, the term of this patent is extended or adjusted under 35 U.S.C. 154(b) by 904 days.

(21) Appl. No.: 15/648,531

(22) Filed: Jul. 13, 2017

(65) Prior Publication Data
US 2019/0015001 A1   Jan. 17, 2019

(51) Int. Cl.
| | |
|---|---|
| A61B 5/03 | (2006.01) |
| G16H 50/30 | (2018.01) |
| A61B 5/107 | (2006.01) |
| A61M 5/158 | (2006.01) |
| A61M 5/142 | (2006.01) |
| A61B 5/00 | (2006.01) |
| A61B 3/12 | (2006.01) |
| A61M 5/172 | (2006.01) |
| G16H 20/13 | (2018.01) |

(52) U.S. Cl.
CPC .......... *A61B 5/032* (2013.01); *A61B 3/12* (2013.01); *A61B 5/031* (2013.01); *A61B 5/1072* (2013.01); *A61B 5/7275* (2013.01); *A61M 5/158* (2013.01); *A61M 5/1723* (2013.01); *G16H 20/13* (2018.01); *G16H 50/30* (2018.01); *A61B 2503/20* (2013.01); *A61M 5/142* (2013.01); *A61M 2202/0464* (2013.01); *A61M 2205/3331* (2013.01); *A61M 2205/3344* (2013.01)

(58) Field of Classification Search
None
See application file for complete search history.

(56) References Cited

PUBLICATIONS

Wostyn et al. Optic Nerve Sheath Distention as a Protective Mechanism Against the Visual Impairment and Intracranial Pressure Syndrome in Astronauts; iovs.arvojournals.org j ISSN: 1552-5783; 2017 (Year: 2017).*
Hansen et al. Validation of the optic nerve sheath response to changing cerebrospinal fluid pressure: ultrasound findings during intrathecal infusion tests; J Neurosurg 87:34-40, 1997 (Year: 1997).*
Alexander et al. Risk of Spaceflight-Induced Intracranial Hypertension and Vision Alterations; Jul. 12, 2012; National Aeronautics and Space Administration (Year: 2012).*

* cited by examiner

*Primary Examiner* — Kaylee R Wilson
*Assistant Examiner* — Jay B Shah
(74) *Attorney, Agent, or Firm* — Amster, Rothstein & Ebenstein LLP

(57) ABSTRACT

Described herein is the use of the optic nerve sheath (ONS) response to alterations in cerebrospinal fluid (CSF) pressure for predicting the risk of developing Visual Impairment and Intracranial Pressure (VIIP) syndrome in a subject.

14 Claims, No Drawings

BIOMARKERS FOR VISUAL IMPAIRMENT AND INTRACRANIAL PRESSURE (VIIP) SYNDROME

FIELD OF THE INVENTION

The present application relates generally to the field of ophthalmic diseases. The application relates more particularly to Visual Impairment and Intracranial Pressure (VIIP) syndrome and provides predictive biomarkers therefor. More particularly, the present application relates to methods and tools for predicting the risk of developing Visual Impairment and Intracranial Pressure (VIIP) syndrome in a subject.

BACKGROUND

A significant proportion of the astronauts who have participated in long-duration space flights experience ophthalmic abnormalities upon their return. These ophthalmic abnormalities include optic disc edema, optic nerve sheath (ONS) distention, globe flattening, nerve fiber layer thickening, cotton wool spots, choroidal folds, and hyperopic shifts, also designated as Visual Impairment and Intracranial Pressure (VIIP) syndrome. Currently, the exact mechanisms causing the VIIP syndrome are yet to be fully elucidated, but elevated intracranial pressure (ICP) resulting from microgravity-induced cephalad fluid shifts e.g. during a spaceflight, is hypothesized to play an important role (Mader et al. 2011, Ophthalmology 118:2058-2069).

Although it is assumed that all astronauts exposed to microgravity have some degree of ICP elevation in-flight, not all crewmembers have manifested overt signs or symptoms of the VIIP syndrome. It is believed that some crewmembers are more susceptible than others due to interindividual factors such as genetics, anatomical features or physical fitness (Nelson et al. 2014, Life (Basel) 4:621-665).

To be able to identify astronaut candidates who will be able to complete long-duration missions with low risk of the VIIP syndrome, it would be desirable to have biomarkers for VIIP risk prediction.

SUMMARY OF THE INVENTION

The present disclosure provides biomarkers for predicting the risk of developing VIIP syndrome in a subject, in particular in a subject that is exposed or is to be exposed to microgravitiy, based on the optic nerve sheath response to alterations in cerebrospinal fluid pressure. In particular, the inventor considers that inter-individual changes in ONS response to changing CSF pressure correlate with the likelihood of developing VIIP syndrome. More particularly, the present invention is based on the proposition that subjects with lower CSF pressures at saturation of the ONS response and/or lower ONS diameter/CSF pressure ratios are more likely to develop VIIP syndrome.

Accordingly, provided herein is a method of predicting the risk of developing VIIP syndrome in a subject, when said subject would be exposed to microgravity, the method comprising the steps of:
 administering intermittently a composition comprising artificial CSF to the subject via intrathecal infusion;
 measuring CSF pressure in the subject following each intermittent CSF administration;
 measuring the optic nerve sheath (ONS) diameter in the subject following each intermittent CSF administration; and
 determining whether or not the subject is at risk of developing VIIP syndrome, based on the measured CSF pressures and the measured ONS diameters.

In preferred embodiments, the CSF pressure and the ONS diameter are measured at steady-state CSF pressure following each intermittent CSF administration. In embodiments, the ONS diameter is measured by ultrasound.

In embodiments, said intrathecal infusion is ensured by an infusion device comprising an intrathecal needle connected to an infusion pump and a pressure sensor, wherein said infusion pump is connectable to a reservoir for containing the composition comprising artificial CSF, and wherein said pressure sensor is configured to monitor CSF pressure in the subject. In embodiments, the CSF flow rate ranges from 0.1 ml/minute to 8 ml/minute. In preferred embodiments, the CSF flow rate is increased at each intermittent infusion. In further embodiments, the CSF flow rate is increased in steps ranging from 0.25 to 2.00 ml/minute, preferably from 0.5 to 1.00 ml/minute. In embodiments, the administration of each intermittent CSF infusion is until steady-state CSF pressure is reached. In embodiments, each intermittent CSF infusion is administered after CSF pressure returned to basal CSF pressure following cessation of the previous infusion.

In certain embodiments, the method further comprises the step of calculating the ratio between the measured ONS diameter and the measured CSF pressure, and determining whether or not the subject is at risk of developing VIIP syndrome, is based on said ONS diameter/CSF pressure ratio. In further embodiments, an ONS diameter/CSF pressure ratio below 0.040 mm/mm Hg, preferably below 0.035 mm/mm Hg, indicates that the subject is at risk of developing VIIP syndrome.

In other embodiments, determining whether or not the subject is at risk of developing VIIP syndrome, is based on the CSF pressure at saturation of the ONS response. In further embodiments, a CSF pressure at saturation of the ONS response below 45 mm Hg, preferably below 40 mm Hg, indicates that the subject is at risk of developing VIIP syndrome.

In embodiments, said VIIP syndrome is characterized by one or more of optic disc edema, globe flattening, nerve fiber layer thickening, cotton wool spots, choroidal folds and hyperopic shifts. In preferred embodiments, said VIIP syndrome is characterized by at least optic disc edema. Accordingly, in certain embodiments, the method as described herein is for predicting the risk of developing VIIP-associated optic disc edema in a subject.

Also provided herein is a composition comprising artificial cerebrospinal fluid (CSF) for use in a method for predicting the risk of developing VIIP syndrome in a subject, when said subject would be exposed to microgravity, wherein the method comprises the steps of:
 administering intermittently a composition comprising artificial CSF to the subject via intrathecal infusion;
 measuring CSF pressure in the subject following each intermittent CSF administration;
 measuring the optic nerve sheath (ONS) diameter in the subject following each intermittent CSF administration; and
 determining whether or not the subject is at risk of developing VIIP syndrome based on the measured CSF pressures and the measured ONS diameters.

In embodiments, said intrathecal infusion is ensured by an infusion device comprising an intrathecal needle connected to an infusion pump and a pressure sensor, wherein said infusion pump is connectable to a reservoir for containing the composition comprising artificial CSF, and wherein said pressure sensor is configured to monitor CSF pressure in the subject. In embodiments, the CSF flow rate ranges from 0.1 ml/minute to 8 ml/minute. In preferred embodiments, the CSF flow rate is increased at each intermittent infusion. In further embodiments, the CSF flow rate is increased in steps ranging from 0.25 to 2.00 ml/minute, preferably from 0.5 to 1.00 ml/minute. In embodiments, the administration of each intermittent CSF infusion is until steady-state CSF pressure is reached. In embodiments, each intermittent CSF infusion is administered after CSF pressure returned to basal CSF pressure following cessation of the previous infusion.

In certain embodiments, the composition is for use in a method further comprising the step of calculating the ratio between the measured ONS diameter and the measured CSF pressure, and wherein determining whether or not the subject is at risk of developing VIIP syndrome, is based on said ONS diameter/CSF pressure ratio. In further embodiments, an ONS diameter/CSF pressure ratio below 0.040 mm/mm Hg, preferably below 0.035 mm/mm Hg, indicates that the subject is at risk of developing VIIP syndrome.

In other embodiments, the composition is for use in a method, wherein determining whether or not the subject is at risk of developing VIIP syndrome, is based on the CSF pressure at saturation of the ONS response. In further embodiments, a CSF pressure at saturation of the ONS response below 45 mm Hg, preferably below 40 mm Hg, indicates that the subject is at risk of developing VIIP syndrome.

In embodiments, the composition is for use in method, wherein said VIIP syndrome is characterized by one or more of optic disc edema, globe flattening, nerve fiber layer thickening, cotton wool spots, choroidal folds and hyperopic shifts. In preferred embodiments, said VIIP syndrome is characterized by at least optic disc edema. Accordingly, in certain embodiments, the composition is for use in a method of predicting the risk of developing VIIP-associated optic disc edema in a subject.

The above and other characteristics, features and advantages of the present invention will become apparent from the following detailed description, which illustrates, by way of example, the principles of the invention.

DETAILED DESCRIPTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms "first", "second", "third" and the "like" in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the features of the claimed embodiments can be used in any combination.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

The present application generally relates to predicting the risk of Visual Impairment and Intracranial Pressure (VIIP) syndrome in a subject, in particular the risk of developing VIIP syndrome in a subject when said subject would be exposed to microgravity, based on the optic nerve sheath response to alterations in cerebrospinal fluid pressure. More particularly, CSF pressure at saturation of the ONS response and the ratio between the ONS diameter and CSF pressure are provided herein as predictive biomarkers of VIIP syndrome.

As used herein "Visual Impairment and Intracranial Pressure (VIIP)" refers to a condition characterized by ophthalmologic abnormalities, including optic disc edema, globe flattening, nerve fiber layer thickening, cotton wool spots, choroidal folds and/or hyperopic shifts, that is observed in subjects, in particular astronauts, which are or have been exposed to microgravity such as during a spaceflight. Accordingly, when reference is made to "VIIP syndrome" herein, it is intended to denote one or more of optic disc edema, globe flattening, nerve fiber layer thickening, cotton wool spots, choroidal folds and/or hyperopic shifts. In certain embodiments of the methods and compositions for use in the methods as described herein, VIIP syndrome is characterized by at least optic disc edema. Accordingly, in certain embodiments, the methods as described herein are for predicting the risk of developing VIIP-associated optic disc edema.

As used herein, "papilledema" or "papilloedema" or "optic disc edema" or "optic disc swelling" refers to a condition in which increased pressure in or around the brain (i.e. increased intracranial pressure) causes the part of the optic nerve inside the eye to swell. Ophthalmoscopically papilledema appears as a swelling of the axons of the optic nerve head and retinal nerve fiber layer ("NFL"). There may be a twenty-fold thickening of the nerve fibers. Symptoms of papilledema may be fleeting disturbances in vision, headache, vomiting, or a combination thereof.

The terms "Visual Impairment and Intracranial Pressure (VIIP)-associated papilledema" or "spaceflight-induced papilledema" or "microgravity-induced papilledema" as used herein denote papilledema as observed in subjects, in particular astronauts, which are or have been exposed to microgravity.

As used herein, "globe flattening" refers to a deformation, in particular a flattening, of the posterior wall of the eye globe. Globe flattening can be detected by magnetic resonance (MR) imaging.

The terms "choroidal folds" or "chorioretinal folds" refer herein to parallel grooves or striae observed in the fundus. They are seen ophthalmoscopically and on angiography as alternating light and dark streaks oriented horizontally at the posterior pole. Less commonly vertical, oblique, or irregular alignment may be seen.

With the term "hyperopic shift" is meant herein an abnormal condition of the eye in which vision becomes better for distant objects than for near objects.

As used herein, "cotton wool spots" refer to fluffy white patches that are observed on the retina of the eye on funduscopic exam. They are caused by damage to nerve fibers and are a result of accumulations of axoplasmic material within the nerve fiber layer.

In embodiments of the methods and compositions for use in the methods as described herein, the subject is exposed or has been exposed to microgravity (such as an astronaut) or is to be exposed to microgravity (such as a candidate astronaut).

It has been observed (see, Hansen and Helmke, 1997) that at the low-CSF pressure end, a certain threshold CSF pressure needs to be exceeded before changes in ONS diameter occur. Above this threshold, the ONS diameter is directly related to CSF pressure, and at higher CSF pressure levels, the ONS diameter remains constant. This threshold CSF pressure and the CSF pressure at which said ONS saturation occurs varies interindividually, as does the relative change in ONS diameter per CSF pressure unit.

The "ONS saturation" or "saturation of the ONS response" as used herein, refers to the point at which the ONS diameter remains constant, regardless the CSF pressure.

The CSF pressure at which said ONS saturation is reached, is referred to herein as "CSF pressure at ONS saturation" or "CSF pressure at saturation of the ONS response".

The change of ONS diameter per CSF pressure unit is referred to herein as "the ONS diameter/CSF pressure ratio".

Measurement of the ONS diameter and CSF pressure can be done during an infusion test as is known in the art. An infusion test can be performed as described in Cardim et al. (2016 Acta Neurochir 158:279-287). For example, a spinal needle (e.g. 18 G, 3.50 in.) is inserted in the lower lumbar intervertebral segments, e.g. between the lumbar L3/L4 or L4/L5 vertebrae, and it is used for both pressure measurements and fluid infusion. This needle is connected to a pressure transducer, for which the signal is displayed on a monitor and/or recorded on paper or in a computer, and to an infusion pump that can deliver CSF at adjustable flow rates.

Accordingly, provided herein is a method of predicting the risk of developing VIIP syndrome in a subject, the method comprising the steps of:
  administering intermittently CSF to the subject via infusion;
  measuring CSF pressure in the subject following each intermittent CSF administration or infusion;
  measuring the optic nerve sheath (ONS) diameter in the subject following each intermittent CSF administration or infusion; and
  determining whether or not the subject is at risk of developing VIIP syndrome based on the measured CSF pressures and the measured ONS diameters.

Where reference is made to the administration or infusion of CSF herein, it is intended to refer to a CSF-like solution, or to CSF which is (at least partially) of foreign origin (i.e. not from the subject to which it is administered).

A "CSF-like solution" as used herein refers to a solution that consists essentially of CSF or artificial CSF.

The term "artificial CSF" (aCSF) as used herein refers to a solution that closely matches the electrolyte concentrations of cerebrospinal fluid. Typically, the artificial CSF comprises sodium ions at a concentration of 140-190 mM, potassium ions at a concentration of 2.5-4.5 mM, calcium ions at a concentration of 1-1.5 mM, magnesium ions at a concentration of 0.5-1.5 mM, phosphor ions at a concentration of 0.5-1.5 mM, chloride ions a concentration of 100-200 mM. In one example, the artificial CSF comprises sodium ions at a concentration of 150 mM, potassium ions at a concentration of 3 mM, calcium ions at a concentration of 1.4 mM, magnesium ions at a concentration of 0.8 mM, phosphor ions at a concentration of 1 mM, chloride ions a concentration of 155 mM. aCSFs have been described in the art and include, but are not limited to Elliot's solutions A and B and ARTCEREB™.

In the method described herein, CSF can be administered to the cerebral ventricles or to the intrathecal space surrounding the spinal cord. In preferred embodiments, CSF is administered into the intrathecal or subarachnoid space. The term "intrathecal space" also referred to as the subarachnoid space (SAS) is the fluid-filled area located between the innermost layer of covering (the pia mater) of the spinal cord and the middle layer of covering (the arachnoid mater). Indeed, the administration of CSF or a CSF-like solution can be done locally, in the cerebral ventricles, but in most embodiments the same effect can be achieved less invasively by infusion more remotely, i.e. intrathecally anywhere along the spinal cord, including the cervical region, the thoracic region, the lumbar region etc. In embodiments, intrathecal administration or infusion is done in the lumbar region, e.g. in the lower lumbar intervertebral segments such as between the lumbar L3/L4 or L4/L5 vertebrae.

An infusion device suitable for use in the method described herein, i.e. an infusion device suitable for infusing CSF into the intrathecal or subarachnoid space, may comprise an intrathecal needle connected to an infusion pump and a pressure sensor, wherein said infusion pump is connectable to a reservoir for containing a CSF-like solution such as a composition comprising artificial CSF, and wherein said pressure sensor, such as a pressure transducer, is configured to monitor CSF pressure in the subject. Preferably, the flow rate of the infusion pump is adjustable. The infusion pump is preferably configured to ensure a CSF infusion rate in the range from 0.1 to 8 ml/min, preferably from 0.1 to 6 ml/min or from 0.1 to 4 ml/min.

The term "intermittent" means administration that occurs non-continuously or at intervals. As used herein, intermittent administration encompasses administering a plurality (i.e. two or more) of intermittent infusions, with a rest period between two infusions wherein no CSF is administered.

In particular embodiments of the method described herein, the administration of each intermittent CSF infusion is until steady-state CSF pressure is reached. In embodiments, steady-state CSF pressure is reached when fluctuations of CSF pressure are below 4 mm Hg, preferably below 3 mm Hg, most preferably below 2 mm Hg for 2 minutes.

In particular embodiments of the method described herein, each intermittent CSF infusion is administered after CSF pressure returned to basal CSF pressure following cessation of the previous infusion. As used herein "basal CSF pressure" refers to the CSF pressure that is measured in the subject prior to the start of infusion. Basal CSF pressure can be determined in a subject by recording CSF pressure for a period of between 5 min to 15 min, such as for 5 min or for 10 min, prior to initiating CSF infusion.

In preferred embodiments, the CSF flow rate is increased at each intermittent infusion. The CSF flow rate may be increased in steps ranging from 0.25 to 2.00 ml/minute, preferably from 0.50 to 1.00 ml/minute, such as in steps of 0.50 ml/minute or 1.00 ml/minute. The increase in CSF flow rate can be continued as long as the subject remains free of headache, nausea, or mental changes and as long as CSF pressure is below 60 mm Hg.

In embodiments of the method described herein, CSF pressure and ONS diameter are measured at steady-state CSF pressure following each intermittent infusion.

The term "cerebrospinal fluid pressure" or "CSF pressure" as used herein refers to the pressure of cerebrospinal fluid (CSF) within the skull and thus in the brain tissue and cerebrospinal fluid. Cerebrospinal fluid (CSF) flows into the brain ventricles and interconnecting chambers, namely, the cisterns and the subarachnoid space (SAS). CSF is absorbed through the arachnoid villi, located principally over the superior surfaces of the cerebral hemispheres. Some villi also exist at the base of the brain and along the roots of the spinal nerves. The absorptive processes include bulk transport of large molecules and as well as diffusion across porous membranes of small molecules (see, e.g., Adams et al. 1989, Principles of Neurology: 501-502).

CSF pressure can be measured by lumbar puncture. More particularly, CSF pressure can be measured by means of a pressure sensor, such as a pressure transducer, present in an infusion device as described herein. More particularly, CSF pressure is measured by means of a pressure sensor, such as a pressure transducer, which is connected to a intrathecal needle that is inserted into the intrathecal or subarachnoid space of the subject, which allows continuously monitoring CSF pressure in the subject.

Optic nerve sheath (ONS) diameter information can be measured by ultrasound, in particular B-mode ultrasound, or other imaging modalities (e.g., computer tomography or magnetic resonance imaging). In preferred embodiments, ONS diameter is measured by ultrasound. Measurements on the eye are ideally suited for ultrasound because the globe of the eye is fluid filled, which presents a suitable interface and medium for ultrasound to visualize the optic nerve. Moreover, physicians are familiar with ultrasound technology and compared to magnetic resonance imaging ("MRI") and computed tomography ("CT"), ultrasound technology is also relatively inexpensive and portable. ONS diameter is suitably measured approximately 3 mm posterior of the globe, and can be measured using a 7-10 MHz ultrasound probe in a B-mode. Devices designed for the ophthalmology (e.g., devices made by Alcon, Sonomed, and Tomey) are all considered suitable. Hospital bedside ultrasound imaging devices such as the GE Logiq series and Phillips Agilent Image Point series can be used to measure ONS diameter as well.

In certain embodiments, determining whether or not the subject is at risk of developing VIIP syndrome is based on the CSF pressure at saturation of the ONS response.

It is believed that subjects with lower CSF pressures at saturation of the ONS response are more likely to develop VIIP syndrome.

Accordingly, in certain embodiments, a CSF pressure at saturation of the ONS response below 52 mm Hg, below 50 mm Hg or below 48 mm Hg, preferably below 45 mm Hg, such as below 44 mm Hg, below 43 mm Hg, below 42 mm Hg, or below 41 mm Hg, more preferably below 40 mg Hg such as below 39 mm Hg, below 38 mm Hg, below 37 mm Hg, below 36 mm Hg, even more preferably below 35 mm Hg, below 34 mm Hg, below 33 mm Hg, below 32 mm Hg, below 31 mm Hg or below 30 mm Hg indicates that the subject is at risk of developing VIIP syndrome.

It has further been observed that subjects with lower CSF pressures at saturation of the ONS response also had the lower ONS diameter/CSF pressure ratios (see, Hansen and Helmke 1997 J. Neurosurg. 87:34-40). Therefore, in other embodiments, determining whether or not the subject is at risk of developing VIIP syndrome is based on the ONS diameter/CSF pressure ratio. In these embodiments, the method further comprises the step of calculating the ONS diameter/CSF pressure ratio. More particularly, the ONS diameter and CSF pressure are measured at various steady-state levels (i.e. following each intermittent infusion) during an intrathecal infusion test as described elsewhere herein to generate the subject's individual ONS diameter/CSF pressure ratio. Indeed, it has been observed that a linear relationship exist between ONS diameter and CSF pressure within a certain CSF pressure interval, namely beyond the CSF pressure threshold at which the ONS dilates in response to CSF pressure and below the CSF pressure at saturation of the ONS response. Thus, ONS diameter and CSF pressure for calculation of the ONS diameter/CSF pressure ratio are preferably measured within this CSF pressure interval.

Accordingly, in embodiments, it is determined that the subject is at risk of developing VIIP syndrome if the ONS diameter/CSF pressure ratio is below 0.045 mm/mm Hg or below 0.042 mm/mm Hg, preferably below 0.040 mm/mm Hg such as below 0.039 mm/mm Hg, below 0.038 mm/mm Hg, below 0.037 mm/mm Hg, or below 0.036 mm/mm Hg, more preferably below 0.035 mm/mm Hg such as below 0.034 mm/mm Hg, below 0.033 mm/mm Hg, below 0.032 mm/mm Hg, or below 0.031 mm/mm Hg, even more preferably below 0.030 mm/mm Hg, below 0.028 mm/mm Hg, below 0.025 mm/mm Hg, or below 0.020 mm/mm Hg.

In embodiments, determining whether or not the subject is at risk of VIIP syndrome is based on the CSF pressure at saturation of the ONS response and on the ONS diameter/CSF pressure ratio. More particularly, in embodiments it is determined that the subject is at risk of developing VIIP syndrome if the CSF pressure at saturation is below 45 mm Hg and the ONS diameter/CSF pressure ratio is below 0.038 mm/mm Hg, preferably if the CSF pressure at saturation is below 45 mm Hg and the ONS diameter/CSF pressure ratio is below 0.035 mm/mm Hg such as below 0.034 mm/mm Hg or below 0.033 mm/mm Hg.

A related aspect of the present invention is directed to a composition comprising artificial CSF for use in a method of predicting the risk of developing VIIP syndrome in a subject as described herein.

EXAMPLE

Evaluation of the Effect of CSF Pressure at ONS Response on the Risk of Developing VIIP Syndrome In each of the candidate astronauts, ONS diameter and CSF pressure are measured. ONS diameter and CSF pressure can be measured in subjects undergoing intrathecal CSF infusion tests, wherein the CSF pressure is gradually increased. The response of the ONS to increasing CSF pressure is measured. It is established that subjects with lower CSF pressures at saturation of the ONS response are more likely to develop the ophthalmic abnormalities of the VIIP syndrome. Indeed, in these subjects, ONS expansion reaches a maximum capacity more rapidly (at lower CSF pressure) and, once the limits of compensation have been reached, progressively smaller increases in CSF volume are associated with significant increases in CSF pressure in the ONS, resulting in ophthalmic changes including optic disc swelling, globe flattening, nerve fiber layer thickening, cotton wool spots, choroidal folds, and/or hyperopic shifts. In particular, the significantly elevated CSF pressure at eye level results in anteriorly directed forces that indent the posterior sclera, resulting in posterior globe flattening, redundancy and folding of the choroid, and axial shortening. In addition, the rise in CSF pressure at eye level causes arrest of orthograde axonal transport from the ganglion cell bodies in the retina toward the brain and the lateral geniculate ganglion, resulting in accumulation of axonal transport materials, ultimately causing optic disc swelling. The significantly increased CSF pressure in the ONS also activates a one-way directional glymphatic (paravascular) flow from the optic nerve to the eye as compensating route for CSF drainage. This imbalance between ocular glymphatic inflow and outflow results in glymphatic stasis predominantly within the prelaminar region of the optic nerve head, which contributes to optic disc edema.

It was further observed that the subjects with lower CSF pressures at saturation of the ONS response also had the lowest ONS diameter/CSF pressure ratios.

Therefore, CSF pressure at saturation of the ONS response, and the ratio between the ONS diameter and CSF pressure are provided herein as predictive biomarkers for VIIP syndrome.

The invention claimed is:

1. A method of predicting a risk of developing Visual Impairment and Intracranial Pressure (VIIP) syndrome in a subject, the method comprising:
    administering a composition comprising artificial cerebrospinal fluid (CSF) to the subject via a plurality of intermittent intrathecal infusions with a CSF flow rate;
    measuring a CSF pressure in the subject following each of said intermittent infusions thereby obtaining a measured CSF pressure;
    measuring an optic nerve sheath (ONS) diameter in the subject following each of said intermittent infusions thereby obtaining a measured ONS diameter;
    calculating a ratio of the measured ONS diameter to the measured CSF pressure, thereby obtaining an ONS diameter/CSF pressure ratio following each of said intermittent infusions; and
    determining whether or not the subject is at risk of developing VIIP syndrome based on said ONS diameter/CSF pressure ratios following each of said intermittent infusions.

2. The method according to claim 1, wherein an ONS diameter/CSF pressure ratio below 0.040 mm/mm Hg indicates that the subject is at risk of developing VIIP syndrome.

3. The method according to claim 1, wherein the VIIP syndrome is characterized by one or more of optic disc edema, globe flattening, nerve fiber layer thickening, cotton wool spots, choroidal folds and hyperopic shifts.

4. The method according to claim 1, wherein the VIIP syndrome is characterized by at least optic disc edema.

5. The method according to claim 1, wherein the CSF pressure and the ONS diameter are measured at steady-state CSF pressure following each of said intermittent infusions.

6. The method according to claim 1, wherein the ONS diameter is measured by ultrasound.

7. The method according to claim 1, wherein said intrathecal infusion is ensured by an infusion device comprising an intrathecal needle connected to an infusion pump and a pressure sensor, wherein said infusion pump is connectable to a reservoir for containing the composition comprising artificial CSF, and wherein said pressure sensor is configured to monitor CSF pressure in the subject.

8. The method according to claim 1, wherein the CSF flow rate is increased at each of said intermittent infusions.

9. The method according to claim 1, wherein the CSF flow rate ranges from 0.1 ml/minute to 8 ml/minute.

10. The method according to claim 1, wherein the administration of said intermittent CSF infusions is continued until steady-state CSF pressure is reached.

11. The method according to claim 8, wherein the CSF flow rate is increased in steps ranging from 0.25 to 2.00 ml/minute.

12. The method according to claim 1, wherein an intermittent CSF infusion is administered after CSF pressure returns to a basal CSF pressure following cessation of a previous infusion.

13. A method of predicting a risk of developing Visual Impairment and Intracranial Pressure (VIIP) syndrome in a subject, the method comprising:
    administering a composition comprising artificial cerebrospinal fluid (CSF) to the subject via a plurality of intermittent intrathecal infusions with a CSF flow rate;
    measuring a CSF pressure in the subject following each of said intermittent infusions, thereby obtaining a measured CSF pressure;
    measuring an optic nerve sheath (ONS) diameter in the subject following each of said intermittent infusions thereby obtaining a measured ONS diameter; and
    wherein a saturation of ONS response is obtained in said subject when the ONS diameter remains constant, determining whether or not the subject is at risk of developing VIIP syndrome based on CSF pressure at saturation of the ONS response.

14. The method according to claim 13, wherein a CSF pressure at saturation of an ONS response below 45 mm Hg indicates that the subject is at risk of developing VIIP syndrome.

* * * * *